US009683977B2

(12) United States Patent
Liu et al.

(10) Patent No.: US 9,683,977 B2
(45) Date of Patent: Jun. 20, 2017

(54) SCHEMA TO REDUCE RF TRAFFIC AND INCREASE THE NETWORK CAPACITY FOR LARGE WIRELESS GAS SENSOR NETWORKS

(71) Applicant: Honeywell International Inc., Morristown, NJ (US)

(72) Inventors: James Li Liu, Livermore, CA (US); Kai Ren, Shanghai (CN)

(73) Assignee: Honeywell International Inc., Morris Plains, NJ (US)

( * ) Notice: Subject to any disclaimer, the term of this patent is extended or adjusted under 35 U.S.C. 154(b) by 97 days.

(21) Appl. No.: 14/476,825

(22) Filed: Sep. 4, 2014

(65) Prior Publication Data
US 2016/0069851 A1 Mar. 10, 2016

(51) Int. Cl.
*G01N 33/00* (2006.01)
*G08B 21/18* (2006.01)
*H04Q 9/00* (2006.01)
*G08B 21/14* (2006.01)

(52) U.S. Cl.
CPC ..... *G01N 33/0063* (2013.01); *G01N 33/0031* (2013.01); *G01N 33/0075* (2013.01); *G08B 21/14* (2013.01); *G08B 21/182* (2013.01); *H04Q 9/00* (2013.01)

(58) Field of Classification Search
None
See application file for complete search history.

(56) References Cited

U.S. PATENT DOCUMENTS

| 4,340,885 A | * | 7/1982 | Chavis | G08B 17/117 340/632 |
| 6,049,283 A | * | 4/2000 | Lindsay | G01N 27/4163 340/632 |

(Continued)

FOREIGN PATENT DOCUMENTS

WO    2013163657 A1    10/2013

OTHER PUBLICATIONS

International Search Report and Written Opinion, PCT Application No. PCT/US15/46788, mailed Nov. 23, 2015, 14 pages.

*Primary Examiner* — Quan-Zhen Wang
*Assistant Examiner* — Chico A Foxx
(74) *Attorney, Agent, or Firm* — Conley Rose, P.C.; Kristin Jordan Harkins

(57) ABSTRACT

An apparatus including a wireless transceiver of the gas monitoring processor that receives gas readings and a plurality of gas detectors at different locations within the predetermined geographical area that each periodically measure a current gas level at a respective location of the gas detector wherein for each gas reading of the gas detector, a processor of the gas detector compares the current gas level with a previously measured gas level, if the current gas level is different than the previous gas level, then the gas detector wirelessly transmits a message including the current gas level to the wireless transceiver of the gas monitoring processor and if the current gas level is unchanged from the previous gas level, then the gas detector transmits a beacon message to the wireless transceiver of the gas monitoring processor as an indication that the current gas level is unchanged from the previous gas level.

20 Claims, 1 Drawing Sheet

(56) References Cited

U.S. PATENT DOCUMENTS

| | | | | |
|---|---|---|---|---|
| 6,513,723 B1* | 2/2003 | Mueller | | F23N 5/143 236/46 R |
| 8,559,464 B2* | 10/2013 | Caracas | | H04J 3/0652 370/503 |
| 8,804,599 B2* | 8/2014 | Yanagihara | | H04W 84/18 370/315 |
| 9,036,489 B2* | 5/2015 | Huseth | | H04W 52/0206 370/244 |
| 2002/0075146 A1* | 6/2002 | Saheki | | B60C 23/0408 340/447 |
| 2005/0233789 A1* | 10/2005 | Maekawa | | H04L 12/12 463/1 |
| 2007/0131882 A1* | 6/2007 | Richman | | G01J 3/4338 250/573 |
| 2010/0025241 A1* | 2/2010 | Hane | | G01N 27/4074 204/432 |
| 2010/0177684 A1* | 7/2010 | Kore | | H04W 84/18 370/328 |
| 2011/0161044 A1* | 6/2011 | Gonia | | G01S 5/0289 702/150 |
| 2011/0161885 A1* | 6/2011 | Gonia | | G08B 17/10 715/847 |
| 2011/0248857 A1* | 10/2011 | Rutherford | | G08B 21/16 340/632 |
| 2013/0047035 A1* | 2/2013 | Edwards | | G06F 11/3051 714/37 |
| 2013/0170432 A1* | 7/2013 | O'Brien | | H04W 4/06 370/328 |
| 2013/0336292 A1* | 12/2013 | Kore | | G08B 17/10 370/336 |
| 2015/0002274 A1* | 1/2015 | Sengstaken, Jr. | | G06K 7/10009 340/10.34 |
| 2015/0119054 A1* | 4/2015 | Morioka | | H04W 76/02 455/450 |
| 2015/0349877 A1* | 12/2015 | Cirker | | H04B 7/24 370/311 |
| 2016/0044460 A1* | 2/2016 | Cornaby | | H04W 4/023 455/456.3 |
| 2016/0254979 A1* | 9/2016 | Inoue | | H04L 43/0882 |

* cited by examiner

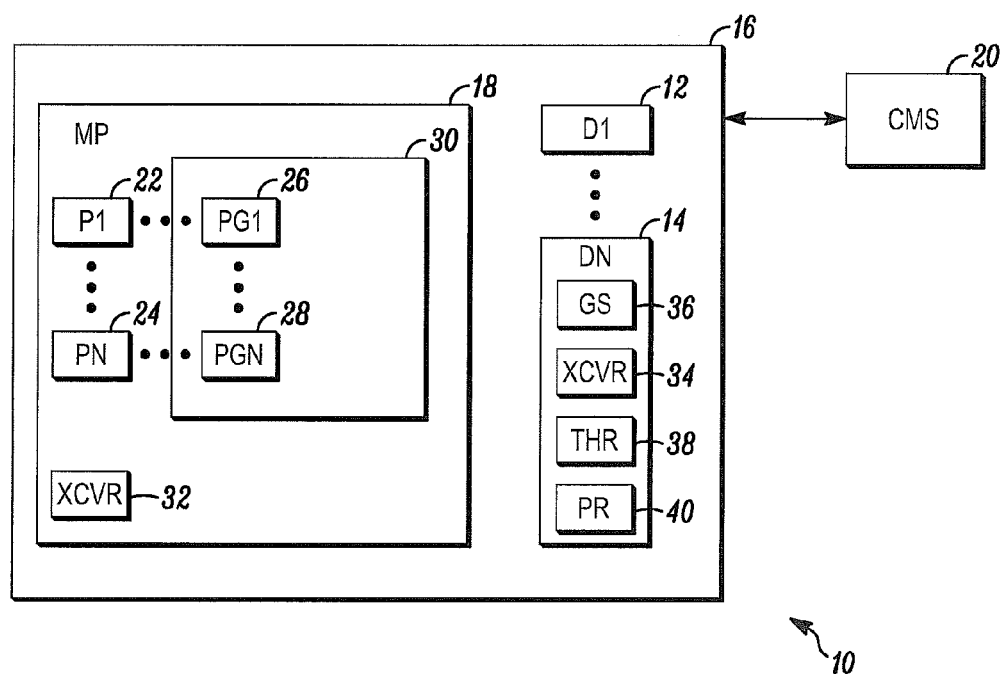

SCHEMA TO REDUCE RF TRAFFIC AND INCREASE THE NETWORK CAPACITY FOR LARGE WIRELESS GAS SENSOR NETWORKS

FIELD

This application relates to security systems and more particular to gas detection systems.

BACKGROUND

Systems are known to protect people and assets from gas leaks within secured areas. Such systems are typically based upon the use of one or more gas sensors distributed throughout the secured area.

For example, carbon monoxide detectors may be located near sleeping areas in residences. Similarly, smoke or carbon monoxide detectors may be placed in a kitchen or near a home's heating system.

In an industrial setting involving the use of a toxic gas, one or more gas detectors may be placed near a source and point of consumption of the toxic gas. Carbon monoxide and/or smoke detectors may also be located throughout the area for the protection of people.

In some cases, gas detectors are constructed as integral units. Integral, in this case, means that each gas detector has its own audible alarm and operates independently of any other gas detector.

Alternatively, gas detectors within an area may be coupled to a central monitoring panel. In this case, each gas detector may periodically measure a gas level proximate the device and report its readings to the central monitoring panel. The central monitoring system may receive a gas reading from each gas detector and sound a general (or local) alarm if the detected gas exceeds some threshold level 38.

While such systems work well, they are often difficult to implement. For example, some areas may have hundreds of gas detectors. In such cases, it is difficult for a central monitoring system to reliably receive a reading from each detector and act upon those readings in an expeditious manner. Accordingly, a need exists for better methods of interconnecting gas detectors and central monitoring panels.

BRIEF DESCRIPTION OF THE DRAWINGS

FIG. 1 illustrates a block diagram of a system in accordance herewith.

DETAILED DESCRIPTION

While disclosed embodiments can take many different forms, specific embodiments thereof are shown in the drawings and will be described herein in detail with the understanding that the present disclosure is to be considered as an exemplification of the principles thereof as well as the best mode of practicing same, and is not intended to limit the application or claims to the specific embodiment illustrated.

FIG. 1 is a block diagram of a gas monitoring system 10 shown generally in accordance with an illustrated embodiment. Included within the system is a number of gas detectors 12, 14 used to protect a secured geographic area 16.

The gas detectors may be constructed to detect any of a number of different gases based upon the threat posed to people and/or assets within the secured area. For example, at least some of the detectors may measure a level of carbon monoxide in the case where people area present within the area. Alternatively, at least some other of the detectors may be constructed to measure explosion risk (e.g., from natural gas, ammonia, etc.). Still others may be constructed to detect fires based upon combustion byproducts other than carbon monoxide.

The gas detectors may be monitored by a monitoring and alarm panel 18. Upon detecting dangerous levels of a gas within the secured area, the monitoring panel may sound a local alarm.

The alarm panel may also compose and send an alarm message to a central monitoring station 20. The central monitoring station may respond by summoning help (e.g., the fire department, paramedics, etc.).

Included within the monitoring panel and each of the gas detectors may be one or more processor apparatus 22, 24, each operating under control of one or more computer programs 26, 28 loaded from a non-transitory computer readable medium (memory) 30. As used herein, reference to a step performed by a computer program is also reference to the processor that executed that step.

Included within each of the gas detectors and the monitoring panel is a radio frequency transceiver 32, 34. Upon activation of the system the transceiver of the monitoring panel may synchronize with and form a wireless connection with each of the gas detectors through the corresponding wireless transceiver of the gas detector.

The wireless connection between the monitoring panel and each of the gas detectors may be encrypted. Encryption in this case involves the use of a public key and a private key (e.g., AES128).

The wireless connection may be direct or may be implemented via a mesh network. Where implemented as a mesh network, gas detectors that are out of range of the monitoring panel may use other gas detectors to relay their signals to the monitoring panel and visa versa.

During normal operation, a gas sensor 36 within each of the gas detectors may measure a gas level in the area proximate the gas detector. A gas level detection processor within the gas detector may retrieve the reading from the gas sensor and compare the reading with a previous reading 40. If the reading has changed, a communication processor may transmit the reading through the wireless connection to a monitoring processor within the monitoring panel.

In general, radio frequency (rf) bandwidth is a significant bottleneck in gas detection systems having large numbers of wireless gas detectors. To reduce the network traffic and increase the network capacity, the wireless sensor network of FIG. 1 can use a pushing schema instead of polling. Pushing in this case can be used to easily double the capacity of the network. However, even in the case of a wireless network where data is pushed by each gas detector to the monitoring panel, the network size is limited by the size of the data packet that is wirelessly transmitted to the monitoring panel.

Typically, the rf data rate for gas detectors using an ISM band, 900 MHz system is about 20 kilobits per second (kbs) or lower. With this throughput, only around 100 gas detectors could theoretically be networked. This is based upon a calculated data rate of 120 bytes per data packet, a transmission rate of 20 kbs, the assumption that each gas detector provides an updated reading to the monitoring panel every 30 seconds and that the system uses a mesh network including 5 hops among repeating gas detectors between a reporting, distal gas detector and the monitoring panel.

Accordingly, for a large wireless network with more than 100 nodes (i.e., gas detectors), two rf networks would be needed. In this case, the second network would have a different network identifier and channel.

The system of FIG. 1 uses an approach that significantly reduces network traffic during normal operation. Network traffic is reduced by having each detector operate under one of two different modes based upon the gas reading from the gas sensor. For example, for a gas detector having six sensors, the data packet (payload) to the monitoring panel can be as large as 100 bytes. It may also have up to 20 bytes extra payload for the packet header (package head) and security head information. Based upon these assumptions, a conventional gas detector would transmit 120 bytes every 30 seconds.

In contrast, the gas detectors of the system of FIG. 1 do not need to transmit a complete 120 byte packet every 30 seconds. Instead, the data packet may be much smaller based upon changes detected in the gas reading at the respective gas sensors. For example, if the readings from all of the sensors of any particular gas detector have not changed since a previous reading 40, then the gas detector only sends a beacon signal (beacon information). If the readings continue to be unchanged for some time period, then the gas sensor broadcasts the beacon every 30 seconds. The beacon can be as short as a few bytes. This preserves rf bandwidth within the system and can increase network capacity by as much as 10 times.

Furthermore, since the beacon has no critical sensor reading information, the security head of the data packet can be removed. This offloads the burden of intensive decryption from the monitoring processor and increases the monitoring processor's throughput.

In addition to gas readings, a battery charge level may be considered in reducing the data rate. For example, if all gas sensors of a gas detector and the battery charge level have not changed, then the gas detector transmits a beacon to tell the monitoring processor that the current readings are the same as previous readings. When the monitoring processor receives this beacon, the monitoring processor simply recalls the previous data from memory and displays the previous readings on a display of the alarm panel.

If less than all sensors of a multi-sensor gas detector have changed since a previous reading, then the detector only sends a data packet with readings from the sensors that have changed. Similarly, if the battery level has changed, then the gas detector only forwards the new battery level. When the monitoring processor receives this packet, the monitoring processor updates the sensor reading affected. For sensor readings that have not changed, the monitoring processor simply retrieves a previous reading from memory and uses the previous reading as a current reading.

On the other hand, if one or more sensor readings have changed and the level of at least one exceeds the alarm threshold value, then a data packet with an alarm flag set will be sent to the monitoring processor. The monitoring processor will display the reading and show an alarm indicator on its display.

If one or more sensor readings have changed and have triggered an alarm, a repetition rate of packet transmission will automatically change to a fast pace. For example, the repetition rate may change from 30 seconds to 10 seconds.

When a gas detector only transmits a beacon, there is no reason to perform encryption of the broadcast beacon (e.g., under AES128). This reduces that package size of the components and eliminates the need for encryption/decryption on the gas detector and monitoring processor side of the system.

In general, the system of FIG. 1 includes a gas monitoring processor that monitors gas readings within a predetermined geographic area, a wireless transceiver of the gas monitoring processor that receives gas readings and a plurality of gas detectors at different locations within the predetermined geographical area that each periodically measure a current gas level at a respective location of the gas detector wherein for each gas reading of the gas detector, a processor of the gas detector compares the current gas level with a previously measured gas level, if the current gas level is different than the previous gas level, then the gas detector wirelessly transmits a message including the current gas level to the wireless transceiver of the gas monitoring processor and if the current gas level is unchanged from the previous gas level, then the gas detector transmits a beacon message to the wireless transceiver of the gas monitoring processor as an indication that the current gas level is unchanged from the previous gas level.

Alternatively, the system includes a gas monitoring system that monitors gas readings within a predetermined geographic area and a plurality of gas detectors of the gas monitoring system dispersed within the predetermined geographical area that each periodically measure a current gas level at a respective location of the gas detector wherein for each measured gas reading, the gas detector compares the current gas level with a previously measured gas level, if the current gas level is different than the previous gas level, then the gas detector wirelessly transmits a message including the current gas level to the gas monitoring system and if the current gas level is unchanged from the previous gas level, then the gas detector broadcasts a beacon message as an indication that the current gas level is unchanged from the previous gas level.

Alternatively, the system includes a gas monitoring system that monitors gas readings within a predetermined geographic area and a mesh network including a plurality of gas detectors of the gas monitoring system dispersed within the predetermined geographical area that each periodically measure a current gas level at a respective location of the gas detector wherein for each measured gas reading, the gas detector compares the current gas level with a previously measured gas level, if the current gas level is different than the previous gas level, then the gas detector wirelessly transmits a message including the current gas level through the mesh network to the gas monitoring system and if the current gas level is unchanged from the previous gas level, then the gas detector broadcasts a beacon message as an indication that the current gas level is unchanged from the previous gas level.

From the foregoing, it will be observed that numerous variations and modifications may be effected without departing from the spirit and scope hereof. It is to be understood that no limitation with respect to the specific apparatus illustrated herein is intended or should be inferred. It is, of course, intended to cover by the appended claims all such modifications as fall within the scope of the claims. Further, logic flows depicted in the FIGURES do not require the particular order shown, or sequential order, to achieve desirable results. Other steps may be provided, or steps may be eliminated, from the described flows, and other components may be add to, or removed from the described embodiments.

The invention claimed is:

1. An apparatus comprising:
a plurality of gas detectors at different locations within a predetermined geographical area forming a network, wherein each gas detector of the plurality of gas detectors is configured to periodically measure a gas level at a respective location of the gas detector to provide respective gas readings;
a gas monitoring processor configured to monitor gas levels corresponding to the gas readings within the predetermined geographic area from the plurality of gas detectors; and
a wireless transceiver of the gas monitoring processor configured to receive messages indicative of the gas readings, wherein for each gas reading of a first gas detector of the plurality of gas detectors, a processor of the first gas detector is configured to compare a current gas level with a previously measured gas level,
wherein the first gas detector is configured to wirelessly transmit via a communication processor:
  a message including the current gas level to the wireless transceiver of the gas monitoring processor when the current gas level is different than the previous gas level, and
  a beacon message to the wireless transceiver of the gas monitoring processor as an indication that the current gas level is unchanged from the previous gas level when the current gas level is unchanged from the previous gas level, wherein the beacon message does not include any sensor readings information corresponding to gas readings of the first gas detector, so that the network's traffic is reduced.

2. The apparatus as in claim 1, wherein the processor of the first gas detector is configured to measure a voltage of a battery that powers the first gas detector.

3. The apparatus as in claim 2,
wherein the communication processor of the first gas detector is configured to transmit a battery low voltage message to the gas monitoring processor in place of the beacon message when the voltage of the battery is low and the current level has not changed from the previous gas level.

4. The apparatus as in claim 1, wherein the first gas detector further comprises a plurality of gas sensors associated with a single housing of the first gas detector.

5. The apparatus as in claim 4,
wherein the communication processor is configured to only transmit gas levels that have changed from the plurality of sensors with respect to current gas levels compared to previous gas levels respectively.

6. The apparatus as in claim 1,
wherein the processor of the first gas detector is configured to compare each reading with a threshold value, wherein the communication processor is configured to transmit an alarm message to the gas monitoring processor when the gas reading exceeds the threshold value.

7. The apparatus as in claim 6, wherein the processor of the first gas detector is configured to increase a rate of data transmission to the gas monitoring processor in response to a gas reading exceeding the threshold value.

8. The apparatus as in claim 1, wherein the transmitted beacon message further comprises an unencrypted beacon message without a security header.

9. The apparatus as in claim 1, wherein the gas monitoring processor further comprises a memory containing a previous gas level reading for each of the plurality of gas detectors.

10. The apparatus as in claim 9,
further comprising a processor of the gas monitoring processor that is configured to receive a beacon message from one of the plurality of gas detectors and retrieve a previous gas level reading for that gas detector from the memory, wherein the beacon message does not include any sensor readings information corresponding to gas readings of that gas detector.

11. An apparatus comprising:
a gas monitoring system configured to monitor gas readings within a predetermined geographic area; and
a plurality of gas detectors of the gas monitoring system forming a network, dispersed within the predetermined geographical area that are each configured to periodically measure a gas level at a respective location of the gas detector to provide a respective gas reading, wherein for each measured gas reading, the gas detector is configured to compare a current gas level with a previously measured gas level, wherein the gas detector is configured to wirelessly transmit a message including the current gas level to the gas monitoring system when the current gas level is different than the previous gas level, wherein the gas detector is configured to broadcast a beacon message as an indication that the current gas level is unchanged from the previous gas level when the current gas level is unchanged from the previous gas level, and wherein the beacon message does not include any sensor readings information corresponding to gas readings of the gas detector, so that the network's traffic is reduced.

12. The apparatus as in claim 1, further comprising a processor of the gas monitoring system that is configured, upon receiving the broadcast beacon message from one of the plurality of gas detectors, to retrieve and use a previous gas reading as the current gas reading.

13. The apparatus as in claim 11, wherein at least one of the plurality of gas detectors further comprises a plurality of gas sensors.

14. The apparatus as in claim 11,
wherein the at least one gas detector further comprises a plurality of sensors and a processor that is configured to detect if any of the plurality of sensors have provided a gas reading that is unchanged from a previous gas reading respectively from the plurality of sensors to transmit a beacon message via a communication processor if none of the plurality of sensors have a changed gas reading, wherein the beacon message does not include any sensor readings information corresponding to the plurality of sensors.

15. The apparatus as in claim 14,
wherein the communication processor is configured to only transmit gas readings from respective sensors of the plurality of sensors that have a changed gas level with respect to their current gas reading compared to their respective previous gas reading.

16. The apparatus as in claim 11,
wherein the plurality of gas detectors each further comprise a processor configured to measure a voltage of a battery that powers the gas detector.

17. The apparatus as in claim 11,
wherein the plurality of gas detectors each further comprise a processor configured to transmit a battery low voltage message to the gas monitoring system in place of the beacon message when the battery is low and the gas reading has not changed with respect to the previous gas reading respectively.

18. The apparatus as in claim 11,
wherein the plurality of gas detectors each further comprise a processor configured to compare each gas reading with a threshold value and transmit an alarm message to the gas monitoring system when the gas reading exceeds the threshold value.

19. The apparatus as in claim 18,
wherein the plurality of gas detectors each further comprise a processor configured to increase a rate of data transmission to the gas monitoring system in response to a gas reading exceeding the threshold value.

20. An apparatus comprising:
a gas monitoring system that monitors gas readings within a predetermined geographic area;
a mesh network including a plurality of gas detectors of the gas monitoring system dispersed within the predetermined geographical area that each periodically measure a gas level at a respective location of the gas detector to provide measured gas readings, wherein for each measured gas reading, the gas detector is configured to compare a current gas level with a previously measured gas level, wherein the gas detector is configured to wirelessly transmit a message including the current gas level through the mesh network to the gas monitoring system when the current gas level is different than the previous gas level, wherein the gas detector is configured to broadcast a beacon message as an indication that the current gas level is unchanged from the previous gas level when the current gas level is unchanged from the previous gas level, and wherein the beacon message does not contain any sensor reading information corresponding to gas readings of the gas detector, so that the network's traffic is reduced.

\* \* \* \* \*

UNITED STATES PATENT AND TRADEMARK OFFICE
CERTIFICATE OF CORRECTION

PATENT NO. : 9,683,977 B2  
APPLICATION NO. : 14/476825  
DATED : June 20, 2017  
INVENTOR(S) : James Li Liu and Kai Ren Page 1 of 1

It is certified that error appears in the above-identified patent and that said Letters Patent is hereby corrected as shown below:

In the Drawings

Sheet 1: "FIG. 1" should be added

In the Claims

Column 5, Line 36: "current level" should be "current gas level"

Signed and Sealed this
Seventeenth Day of October, 2017

Joseph Matal
*Performing the Functions and Duties of the
Under Secretary of Commerce for Intellectual Property and
Director of the United States Patent and Trademark Office*